United States Patent
Smith et al.

(10) Patent No.: US 12,285,177 B2
(45) Date of Patent: *Apr. 29, 2025

(54) METHODS AND DEVICES TO REDUCE DAMAGING EFFECTS OF CONCUSSIVE OR BLAST FORCES ON A SUBJECT

(71) Applicants: TBI Innovations, LLC, West Chester, OH (US); Thornhill Research Inc., North York (CA)

(72) Inventors: David Smith, West Chester, OH (US); Joseph A. Fisher, Thornhill (CA)

(73) Assignees: TBI Innovations, LLC, West Chester, OH (US); Thornhill Research Inc., North York (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/328,501

(22) Filed: Jun. 2, 2023

(65) Prior Publication Data
US 2023/0310009 A1      Oct. 5, 2023

Related U.S. Application Data

(63) Continuation of application No. 16/448,847, filed on Jun. 21, 2019, now Pat. No. 11,696,766, which is a (Continued)

(51) Int. Cl.
*A61B 17/00* (2006.01)
*A61B 17/132* (2006.01)
(Continued)

(52) U.S. Cl.
CPC ........ *A61B 17/1325* (2013.01); *A61B 17/135* (2013.01); *A61B 90/08* (2016.02);
(Continued)

(58) Field of Classification Search
CPC ... A61B 17/1325; A61B 17/135; A61B 17/12; A61B 17/1322; A61B 17/132;
(Continued)

(56) References Cited

U.S. PATENT DOCUMENTS

| 428,926 A | 5/1890 | Martin |
| 519,894 A | 5/1894 | Schutz et al. |

(Continued)

FOREIGN PATENT DOCUMENTS

| CA | 2823184 A1 | 4/2012 |
| CA | 3005557 | 5/2017 |

(Continued)

OTHER PUBLICATIONS

Batson, 0. V., "Anatomical Problems Concerned in the Study of Cerebral Blood Flow," Fed. Proc., 3:139-144 (1944).

(Continued)

*Primary Examiner* — Brooke Labranche
*Assistant Examiner* — Christina C Lauer
(74) *Attorney, Agent, or Firm* — Ruggiero McAllister & McMahon LLC

(57) ABSTRACT

A method and device for reducing the damaging effects of a blast or concussive event includes applying pressure to at least one jugular vein to reduce the egress of blood from the cranial cavity during the incidence of the concussive event. Reducing blood out flow from the cranial cavity increases intracranial pressure of the cerebrospinal fluid to reduce the risk of traumatic brain injury and injuries to the spinal column. Reducing blood out flow further increases the intracranial pressure, and thereby increases the pressure of the cochlear fluid, the vitreous humor and the cerebrospinal fluid to thereby reduce the risk of injury to the inner ear, internal structure of the eye and of the spinal column. In addition, increasing intracranial pressure reduces the likeli-
(Continued)

hood of brain injury and any associated loss of olfactory function.

21 Claims, 5 Drawing Sheets

Related U.S. Application Data continuation of application No. 15/150,243, filed on May 9, 2016, now Pat. No. 10,368,877, which is a continuation of application No. 13/489,536, filed on Jun. 6, 2012, now Pat. No. 10,004,515, which is a continuation-in-part of application No. PCT/US2011/055783, filed on Oct. 11, 2011, and a continuation-in-part of application No. 12/931,415, filed on Feb. 1, 2011, now Pat. No. 9,168,045, which is a continuation-in-part of application No. 12/807,677, filed on Sep. 10, 2010, now Pat. No. 8,985,120.

(60) Provisional application No. 61/518,117, filed on Apr. 29, 2011, provisional application No. 61/260,313, filed on Nov. 11, 2009, provisional application No. 61/241,625, filed on Sep. 11, 2009.

(51) Int. Cl.
A61B 17/135 (2006.01)
A61B 90/00 (2016.01)
A61F 5/30 (2006.01)

(52) U.S. Cl.
CPC ....... *A61F 5/30* (2013.01); *A61B 2017/00119* (2013.01); *A61B 2017/00734* (2013.01); *A61B 17/1355* (2013.01); *A61B 2090/0807* (2016.02)

(58) Field of Classification Search
CPC ....... A61B 17/1355; A61B 90/08; A61F 5/32; A61F 5/30
See application file for complete search history.

(56) References Cited

U.S. PATENT DOCUMENTS

| | | | |
|---|---|---|---|
| 1,123,873 A | 1/1915 | Heflin | |
| 1,280,742 A | 10/1918 | Hurd | |
| 1,473,041 A | 11/1923 | Henderson | |
| 1,481,354 A | 1/1924 | Dingfeld | |
| 1,592,496 A | 7/1926 | Madden | |
| 1,691,856 A | 11/1928 | Robbins | |
| 2,091,276 A | 8/1937 | Gilbert | |
| 2,271,927 A | 2/1942 | Saighman | |
| 2,284,205 A | 5/1942 | Hansen | |
| 2,320,183 A | 5/1943 | Martin | |
| 2,385,638 A | 9/1945 | Norwood | |
| 2,676,586 A * | 4/1954 | Coakwell, Jr. | A61B 17/1355 600/19 |
| 2,715,994 A | 8/1955 | Steinacker | |
| 3,008,464 A | 11/1961 | Atkins | |
| 3,078,844 A | 2/1963 | Scholz | |
| 3,171,409 A | 3/1965 | Cetrone | |
| 3,477,425 A | 11/1969 | Grassi | |
| 3,490,448 A | 1/1970 | Grubb | |
| 3,497,872 A | 3/1970 | Mitchell | |
| 3,500,472 A | 3/1970 | Castellani | |
| 3,595,225 A | 7/1971 | Beeman | |
| 3,628,536 A * | 12/1971 | Glesne | A61B 17/1322 606/203 |
| 3,657,739 A | 4/1972 | Holmes, Sr. | |
| 3,765,412 A | 10/1973 | Ommaya et al. | |
| 3,850,164 A | 11/1974 | Hare | |
| 3,901,230 A | 8/1975 | Henkin | |
| 3,945,042 A | 3/1976 | Lobo | |
| 4,121,582 A | 10/1978 | Remiro | |
| 4,159,020 A | 6/1979 | von Soiron et al. | |
| 4,188,946 A | 2/1980 | Watson et al. | |
| 4,243,028 A | 1/1981 | Puyana | |
| 4,272,011 A | 6/1981 | Nagatomo et al. | |
| 4,308,861 A | 1/1982 | Kelly | |
| 4,326,666 A | 4/1982 | Fujiwara et al. | |
| 4,336,807 A | 6/1982 | Benckhuijsen | |
| 4,343,303 A | 8/1982 | Williams | |
| 4,377,159 A | 3/1983 | Hansen | |
| 4,479,495 A | 10/1984 | Isaacson | |
| 4,576,150 A | 3/1986 | Auracher | |
| 4,628,926 A | 12/1986 | Duncan et al. | |
| 4,646,728 A | 3/1987 | Takeda | |
| 4,716,898 A | 1/1988 | Chauve et al. | |
| 4,991,576 A | 2/1991 | Henkin | |
| 4,997,438 A | 3/1991 | Nipper | |
| 5,078,728 A | 1/1992 | Giarratano | |
| 5,152,302 A | 10/1992 | Fareed | |
| 5,255,675 A | 10/1993 | Kolobow | |
| 5,295,949 A | 3/1994 | Hathaway | |
| 5,295,996 A | 3/1994 | Blair | |
| 5,302,806 A | 4/1994 | Simmons et al. | |
| 5,312,350 A | 5/1994 | Jacobs | |
| 5,320,093 A | 6/1994 | Raemer | |
| 5,338,290 A | 8/1994 | Aboud | |
| 5,375,261 A | 12/1994 | Lipke | |
| 5,381,558 A | 1/1995 | Lo | |
| 5,398,675 A | 3/1995 | Henkin et al. | |
| 5,403,266 A | 4/1995 | Bragg et al. | |
| 5,497,767 A | 3/1996 | Olsson et al. | |
| 5,501,697 A | 3/1996 | Fisher | |
| 5,507,280 A | 4/1996 | Henkin et al. | |
| 5,507,721 A | 4/1996 | Shippert | |
| D369,660 S | 5/1996 | Myoga | |
| 5,582,585 A | 12/1996 | Nash-Morgan | |
| 5,584,853 A | 12/1996 | McEwen | |
| 5,601,598 A | 2/1997 | Fisher | |
| 5,643,315 A | 7/1997 | Daneshvar | |
| 5,695,520 A | 12/1997 | Bruckner et al. | |
| 5,709,647 A | 1/1998 | Ferber | |
| 5,752,927 A | 5/1998 | Rogachevsky | |
| 5,792,176 A | 8/1998 | Chang | |
| 5,806,093 A | 9/1998 | Summers | |
| 5,817,218 A | 10/1998 | Hayashi et al. | |
| 5,848,981 A | 12/1998 | Herbranson | |
| 5,940,888 A | 8/1999 | Sher | |
| 5,957,128 A | 9/1999 | Hecker et al. | |
| 5,978,965 A | 11/1999 | Summers | |
| 6,007,503 A | 12/1999 | Berger et al. | |
| D419,267 S | 1/2000 | Hartunian | |
| 6,058,517 A | 5/2000 | Hartunian | |
| 6,158,434 A | 12/2000 | Lugtighcid et al. | |
| 6,165,105 A | 12/2000 | Boutellier | |
| 6,217,601 B1 | 4/2001 | Chao | |
| 6,227,196 B1 | 5/2001 | Jaffe et al. | |
| 6,238,413 B1 | 5/2001 | Wexler | |
| 6,245,024 B1 | 6/2001 | Montagnino et al. | |
| 6,274,786 B1 | 8/2001 | Heller | |
| 6,344,021 B1 | 2/2002 | Juster et al. | |
| 6,354,292 B1 | 3/2002 | Fisher | |
| 6,398,749 B1 | 6/2002 | Slautterback | |
| 6,423,020 B1 | 7/2002 | Koledin | |
| 6,554,787 B1 | 4/2003 | Griffin et al. | |
| D475,139 S | 5/2003 | Myoga | |
| 6,558,407 B1 | 5/2003 | Ivanko et al. | |
| 6,612,308 B2 | 9/2003 | Fisher et al. | |
| 6,622,725 B1 | 9/2003 | Fisher et al. | |
| 6,623,835 B2 | 9/2003 | Chang | |
| 6,655,382 B1 | 12/2003 | Kolobow | |
| 6,659,689 B1 | 12/2003 | Courtney et al. | |
| 6,663,653 B2 | 12/2003 | Akerfeldt | |
| 6,700,031 B1 | 3/2004 | Hahn | |
| 6,711,750 B1 | 3/2004 | Yoo | |
| 6,763,525 B1 | 7/2004 | Spector | |
| 6,766,570 B1 | 7/2004 | Klemm et al. | |
| 6,799,570 B2 | 10/2004 | Fisher | |
| 6,802,841 B2 | 10/2004 | Narimatsu | |
| 6,854,134 B2 | 2/2005 | Cleveland | |
| 7,069,598 B1 | 7/2006 | Welch | |

(56) References Cited

U.S. PATENT DOCUMENTS

| | | | |
|---|---|---|---|
| 7,100,251 B2 | 9/2006 | Howell | |
| 7,100,606 B2 | 9/2006 | Fisher | |
| 7,141,031 B2 | 11/2006 | Garth et al. | |
| D539,425 S | 3/2007 | Harrison | |
| 7,207,953 B1 | 4/2007 | Goicaj | |
| D555,836 S | 11/2007 | Foust et al. | |
| 7,452,339 B2 | 11/2008 | Mattison | |
| 7,618,386 B2 | 11/2009 | Nordt, III et al. | |
| 7,653,948 B2 | 2/2010 | Schwenner | |
| D653,018 S | 1/2012 | Webbe et al. | |
| 8,109,963 B1 | 2/2012 | Korrol | |
| 8,376,975 B1 * | 2/2013 | Harris, Jr. | A61F 13/04 602/17 |
| 8,381,362 B2 | 2/2013 | Hammerslag et al. | |
| 8,900,169 B2 | 12/2014 | Smith et al. | |
| 8,955,165 B1 | 2/2015 | Romero | |
| 8,985,120 B2 * | 3/2015 | Smith | A41D 13/0512 606/204.15 |
| 9,168,045 B2 | 10/2015 | Smith et al. | |
| 9,173,660 B2 | 11/2015 | Smith et al. | |
| D763,518 S | 8/2016 | Fletcher et al. | |
| 9,913,501 B1 | 3/2018 | Flug | |
| 10,004,515 B2 * | 6/2018 | Smith | A61B 17/135 |
| 10,368,877 B2 * | 8/2019 | Smith | A61F 5/30 |
| 10,905,180 B1 | 2/2021 | Minaev et al. | |
| 11,696,766 B2 * | 7/2023 | Smith | A61B 90/08 606/202 |
| 2003/0130690 A1 | 7/2003 | Porrata et al. | |
| 2004/0127937 A1 | 7/2004 | Newton | |
| 2004/0128744 A1 | 7/2004 | Cleveland | |
| 2004/0243044 A1 | 12/2004 | Penegor et al. | |
| 2004/0267178 A1 | 12/2004 | Benckendorff | |
| 2005/0262618 A1 | 12/2005 | Musal | |
| 2006/0015048 A1 | 1/2006 | Pillai | |
| 2006/0122550 A1 | 1/2006 | Weaver | |
| 2006/0048293 A1 | 3/2006 | Lewis et al. | |
| 2006/0095072 A1 | 5/2006 | TenBrink et al. | |
| 2006/0142675 A1 | 6/2006 | Sargent | |
| 2006/0200195 A1 | 9/2006 | Yang | |
| 2007/0033696 A1 | 2/2007 | Sellier | |
| 2007/0060949 A1 | 3/2007 | Curry et al. | |
| 2007/0260167 A1 | 11/2007 | Heart | |
| 2008/0021498 A1 | 1/2008 | Di Lustro | |
| 2008/0071202 A1 | 3/2008 | Nardi et al. | |
| 2008/0132820 A1 | 6/2008 | Buckman et al. | |
| 2008/0200853 A1 | 8/2008 | Tielve | |
| 2008/0319473 A1 | 12/2008 | Rosenbaum | |
| 2009/0076421 A1 | 3/2009 | Grant, Jr. | |
| 2009/0099496 A1 | 4/2009 | Heegaard et al. | |
| 2009/0105625 A1 | 4/2009 | Kohner et al. | |
| 2009/0131973 A1 | 5/2009 | Zacharias | |
| 2009/0143706 A1 | 6/2009 | Acosta | |
| 2009/0173340 A1 | 7/2009 | Lee | |
| 2009/0192423 A1 | 7/2009 | Halmos | |
| 2009/0234261 A1 | 9/2009 | Singh | |
| 2009/0299242 A1 | 12/2009 | Hasegawa | |
| 2010/0000548 A1 | 1/2010 | Haworth et al. | |
| 2010/0042138 A1 | 2/2010 | Duelo Riu | |
| 2010/0071169 A1 | 3/2010 | Williams et al. | |
| 2010/0088808 A1 | 4/2010 | Rietdyk et al. | |
| 2010/0122404 A1 | 5/2010 | Bowlus et al. | |
| 2010/0137768 A1 | 6/2010 | Thorgilsdottir et al. | |
| 2010/0139671 A1 | 6/2010 | Tull et al. | |
| 2010/0152771 A1 | 6/2010 | Di Lustro | |
| 2010/0179586 A1 | 7/2010 | Ward et al. | |
| 2011/0010829 A1 | 1/2011 | Norman | |
| 2011/0028934 A1 | 2/2011 | Buckman et al. | |
| 2011/0040265 A1 | 2/2011 | Lu et al. | |
| 2011/0093003 A1 | 4/2011 | Lee | |
| 2011/0107492 A1 | 5/2011 | Hinchey et al. | |
| 2011/0257571 A1 | 10/2011 | Fritsch et al. | |
| 2011/0270299 A1 | 11/2011 | Rose et al. | |
| 2011/0295174 A1 | 12/2011 | Richards | |
| 2011/0295311 A1 | 12/2011 | Adelman | |
| 2012/0078157 A1 | 3/2012 | Ravikumar et al. | |
| 2012/0197290 A1 | 8/2012 | Smith et al. | |
| 2012/0246974 A1 | 10/2012 | Hammerslag et al. | |
| 2013/0041303 A1 | 2/2013 | Hopman et al. | |
| 2013/0055492 A1 | 3/2013 | Husain | |
| 2013/0085426 A1 | 4/2013 | Brodsky | |
| 2013/0239310 A1 | 9/2013 | Flug | |
| 2013/0274638 A1 | 10/2013 | Jennings et al. | |
| 2013/0333708 A1 | 12/2013 | Hassan | |
| 2014/0031781 A1 | 1/2014 | Razon-Domingo | |
| 2014/0142616 A1 | 5/2014 | Smith | |
| 2014/0276278 A1 | 9/2014 | Smith et al. | |
| 2014/0277101 A1 | 9/2014 | Smith et al. | |
| 2014/0343599 A1 | 11/2014 | Smith et al. | |
| 2015/0305751 A1 | 10/2015 | Hoff et al. | |
| 2016/0044981 A1 | 2/2016 | Frank et al. | |
| 2016/0045203 A1 | 2/2016 | Pollock | |
| 2016/0213381 A1 | 7/2016 | Zhadkevich | |
| 2016/0317160 A1 | 11/2016 | Smith et al. | |
| 2017/0215769 A1 | 8/2017 | Lu et al. | |
| 2017/0215795 A1 | 8/2017 | Ahmad et al. | |
| 2020/0330323 A1 | 10/2020 | Jolly et al. | |
| 2021/0254179 A1 | 8/2021 | Xu et al. | |

FOREIGN PATENT DOCUMENTS

| | | |
|---|---|---|
| CN | 201189186 | 2/2009 |
| CN | 101690658 | 4/2010 |
| CN | 202618320 U | 12/2012 |
| CN | 103385555 | 11/2013 |
| CN | 103385555 A | 11/2013 |
| DE | 3409335 | 9/1985 |
| EP | 0067622 | 12/1982 |
| EP | 2777411 | 9/2014 |
| FR | 719730 | 2/1932 |
| FR | 2041596 | 1/1971 |
| GB | 291600 | 6/1928 |
| GB | 1282097 | 7/1972 |
| JP | 42002568 | 10/1963 |
| JP | S4814547 | 4/1973 |
| JP | S4499310 | 9/1975 |
| JP | S5429876 | 3/1979 |
| JP | S5438272 | 3/1979 |
| JP | S559202 | 1/1980 |
| JP | S5511002 | 1/1980 |
| JP | S6266102 | 3/1987 |
| JP | H0207814 | 1/1990 |
| JP | H11247001 | 9/1999 |
| JP | 2003135472 | 5/2003 |
| JP | 2003-235816 | 8/2003 |
| JP | 3098099 | 2/2004 |
| JP | 2004337393 | 12/2004 |
| JP | 2004036067 | 5/2005 |
| JP | 2005-273094 | 10/2005 |
| JP | 2005292006 | 10/2005 |
| JP | 3171026 | 10/2011 |
| WO | 196620783 | 7/1996 |
| WO | 98/46144 | 10/1998 |
| WO | 2003020061 | 3/2003 |
| WO | 2010056280 | 5/2010 |
| WO | 2011/048518 A1 | 4/2011 |
| WO | 2012/054262 A1 | 4/2012 |
| WO | 2012/156335 A1 | 11/2012 |
| WO | 2012/168449 A1 | 12/2012 |
| WO | 2013/055409 A1 | 4/2013 |
| WO | 2013055409 | 4/2013 |
| WO | 2014143853 | 9/2014 |
| WO | 2015061663 | 4/2015 |
| WO | 2017172964 | 10/2017 |
| WO | 2020005409 | 1/2020 |
| WO | 2020008500 | 1/2020 |
| WO | 2020048518 | 3/2020 |
| WO | 2020051545 | 3/2020 |
| WO | 2020054262 | 3/2020 |
| WO | 2020055409 | 3/2020 |
| WO | 2020056280 | 3/2020 |
| WO | 2020061663 | 4/2020 |
| WO | 2020074350 | 4/2020 |
| WO | 2020143853 | 7/2020 |
| WO | 2020150966 | 7/2020 |

(56) References Cited

FOREIGN PATENT DOCUMENTS

| WO | 2020152649 | 7/2020 |
|---|---|---|
| WO | 2020156335 | 8/2020 |
| WO | 2020168449 | 8/2020 |
| WO | 2020172964 | 9/2020 |
| WO | 202000672 | 10/2020 |

OTHER PUBLICATIONS

Cardoso, A. V., et al., "Microplate Reader Analysis of Triatomine Saliva Effect on Eyrthrocyte Aggregation," Materials Research, 10(1):31-36 (2007).

Ferguson, J., et al., "Cervical collars: a potential risk to the head-injured patient," Injury, 24(7):454-456 (1993) printed in Great Britain.

Finnie, J.W., et al., "Animal Models, Traumatic Brain Injury," Vet Pathol. 39:679-689 (2002).

Gilland, 0., et al., "A Cinemyelographic Study of Cerebrospinal Fluid Dynamics," American journal of Roentgenology, 106(2):369-375 (Jun. 1969).

Gregg, D. E., et al., "Experimental Approaches to the Study of the Cerebral Circulation," Fed. Proc., 3:144-151 (1944).

Kitano, M., et al., "The Elasticity of the Cranial Blood Pool," Journal of Nuclear Medicine, 5:613-625 (1964).

May, P. R.A., et al., "Woodpecker Drilling Behavior, An Endorsement of the Rotational Theory of Impact Brain Injury," Arch. Neurol., 36:370-373 (1979).

Moyer, J., et al., "Effect of increased jugular pressure on cerebral hemodynamic," Journal of Applied Phvsioloav, 7(3):245-247 (1954).

Templer, D. I., et al., "Preventable Brain Damage, Brain Vulnerability and Brain Health," Part I: Impact Damage; ECT and Permanent Brain Damage, Springer Publishing Company, New York pp. 95-107 (1992).

Torres, F., et al., "Changes in the electroencephalogram and in systemic blood pressure associated with carotid compression," Neurology, 20:1077-1083 (Nov. 1970).

Tyrrell, D.A.J., et al., "Observations on the C.S.F. Pressure During Compression of the Jugular Veins," Postarad. Med. J., 27(210): 394-395 (Aug. 1951).

Vannucci, R.C., et al., "Carbon dioxide protects the perinatal brain from hypoxic-ischemic damage: an experimental study in the immature rat," Pediatrics, Abstract from 95(6):868-874 (Jun. 1995).

Boeing "Airplane Vibration" Boeing Aero Magazine, No. 16, Oct. 2001.

Ilic et al "Potential Connections of Cockpit Floor Seat on Passive Vibration Reduction at a Piston Propelled Airplane" Technical Gazette 21, 3(2014) 471-478.

Terhardt "Dominant Spectral Region" The Wayback Machine, Feb. 20, 2000, https://web.archive.org/web/20120426090422/http://www.mmk.e-technik.tu-muench . . . .

Walusinski et al. "How Yawning Switches the Default-Mode Network to the Attentional Network by Activating the Cerebrospinal Fluid Flow" Clinical Anatomy 27:20// 209 (2014).

Hartlage"Brain Injury from Motor Vehicle Accidents, Preventable Damage: Brain Vulnerability and Brain Health" New York: Springer Publishing Company1992.

Leonard "Comparison of central venous and external jugular venous pressures during repair of proximal femoral fracture" British Journal of Anaesthesia (2008), vol. 101, No. 2, pp. 166-170.

Vasavada et al "Head and Neck Anthropometry, Vertebral Geometry and Neck Strength in Height-Matched Men and Women" J. Biomechanics, 41 (2008) 114-121.

Omalu "Concussions and NFL: How the name CTE came about" CNN, Dec. 22, 2016.

Orcutt"New Collar Promises to Keep Athletes Brains from "Sloshing" During Impact" MIT Technology Review, Feb. 3, 2017.

Performance Sports Group Ltd., "Performance Sports Group and Leading Medical Experts Unveil First-of-its-Kind Technology to Address Mild Traumatic Brain Injury" PR Newswire, Nov. 17, 2015.

Baum:"St. X, Moeller aid in concussion prevention study" Cincinnati.com, Jan. 8, 2016.

Brain Injury Association of America Transportation-related incidents are leading cause of brain injury www.biausa.org; Apr. 2001.

\* cited by examiner

METHODS AND DEVICES TO REDUCE DAMAGING EFFECTS OF CONCUSSIVE OR BLAST FORCES ON A SUBJECT

CROSS-REFERENCE TO RELATED APPLICATIONS

This application is a continuation of U.S. application Ser. No. 16/448,847, filed Jun. 21, 2019, which is a continuation of U.S. application Ser. No. 15/150,243, filed May 9, 2016, now U.S. Pat. No. 10,368,877, which is a continuation of U.S. application Ser. No. 13/489,536, filed Jun. 6, 2012, now U.S. Pat. No. 10,004,515, which is a continuation-in-part of U.S. application Ser. No. 12/931,415, filed Feb. 1, 2011, now U.S. Pat. No. 9,168,045, which is a continuation-in-part of U.S. application Ser. No. 12/807,677, filed Sep. 10, 2010, now U.S. Pat. No. 8,985,120, which claims benefit of U.S. Provisional Patent Application No. 61/241,625, filed Sep. 11, 2009, and U.S. Provisional Application No. 61/260,313, filed Nov. 11, 2009. U.S. application Ser. No. 13/489,536 also is a continuation-in-part of PCT Application No. PCT/US2011/055783, filed Oct. 11, 2011, which claims benefit of U.S. Provisional Patent Application No. 61/518,117, filed Apr. 29, 2011, all of which are incorporated by reference herein in their entirety for all purposes.

TECHNICAL FIELD

The present disclosure is generally related to methods and devices for reducing the effects of exposure to concussive events.

BACKGROUND

Traumatic brain injury (TBI) continues to be one of the most common causes of death and morbidity in persons under age 45, even in western societies. A reported 1.7 million people suffer from TBI annually in the U.S. alone, resulting in an estimated per annum total cost of over $60 billion. Historically, prevention of skull and brain injury has focused on the use of helmets as external cranial protection. This approach is fundamentally flawed as helmets have provided benefit for only major penetrating brain injuries and skull fractures. These occur in a very small fraction of head injuries in civilian sphere. Military statistics have shown that even on the battlefield, less than 0.5% of TBI is from a penetrating object. However, both military personnel and athletes are subjected to high velocity, acceleration-deceleration mechanisms that are not mitigated by helmets and lead to concussive injury to the brain. In large part, the human brain's relative freedom of movement within the cranial cavity predisposes to both linear and rotational force vectors, with resultant energy absorption resulting in cellular disruption and dysfunction, sometimes with delayed cell death.

The skull and spinal canal contains only nervous tissue, connective tissue and fat cells and their interstitium, blood, and cerebrospinal fluid (CSF). These fluid contents do not completely fill the rigid container delimited by the skull and bony spinal canal, leaving a 'reserve volume'. The change in volume inside a container for a given change in pressure is termed 'compliance'. Increases in volume of the contents of the skull and bony spinal canal, within the range of reserve volume, occur at low container pressures (due to the high compliance of the system). In the presence of reserve volume, as is seen in a normal physiologic state, acceleration to the skull can result in a differential acceleration between the skull and its contents. As a consequence, the brain and fluids collide with themselves and the inside of the skull. Considering the semi-solid properties of the mammalian brain, this effect is referred to as "SLOSH".

While helmets are effective in preventing the infrequent penetration or fracture of the skull, they have little ability to limit SLOSH effects. Mitigating SLOSH by filling the reserve volume (exhausting compliance) can, therefore, significantly reduce the propensity for differential motion between the skull and its contents, and between the various contents of the skull. By mitigating SLOSH, an accelerating force to the skull would tend to move the skull and its contents in unison, preventing collisions amongst intracranial contents and, therefore, avoiding brain kinetic, acoustic, thermal, and vibrational energy absorption.

The same concussive events that produce TBI can also have damaging effects to the inner ear, spinal cord and structures of the eye. Sensory neural hearing loss is noted to occur at a rate of 85% in TBI. Concurrent injuries to the auditory system as a result of acute blast trauma and resultant traumatic brain injury accounted for one-quarter of all injuries among marines during Operation Iraqi Freedom through 2004—the most common single injury type. Auditory dysfunction has become the most prevalent individual military service-connected disability, with compensation totaling more than $1 billion annually.

Although one might expect blast waves to cause tympanic membrane rupture and ossicular disruption (thus resulting in conductive hearing loss), available audiology reports showed that pure sensory neural loss was the most prevalent type of hearing loss in patients. An observational study performed from 1999-2006 found that 58 percent of active-duty soldiers who complained of hearing loss were diagnosed with pure sensorineural loss. Data from this study also revealed that 38 percent of the patients with blast related TBI reported sensory neural tinnitus (ringing in the ears).

The sites for sensory neural hearing loss are the inner ear structures referred to as the cochlea and vestibular apparatus (semicircular canals). Both of these structures are fluid filled and therefore particularly susceptible to SLOSH induced energy absorption. The tympanic and vestibular canals of the cochlea are also fluid filled and transmit pressure and fluid waves to the delicate hair cells of the organ of cord. The auditory hair cells react directly to the vibrations in the liquid in which they are immersed rather than to transverse vibrations in the cochlear duct. The cochlea and its associated hair cells are particularly susceptible to SLOSH energy absorption.

Approximately 30 ml (21%) of a total CSF volume of 140 ml resides within the spinal axis, and about one-third of the compliance of the CSF system has been attributed to the spinal compartment. The spinal compartment may be likened to a cylindrical container, partially filled with water, with strands of spaghetti (spinal cord tracts) suspended within the water. A container that is fully filled with water can endure much greater compressive loads than the partially filled container. Moreover, the spaghetti suspended in a partially filled container can be severely damaged by SLOSH within the can. Likewise, the spinal compartment can endure higher axial loads and the incidence of SLOSH is greatly minimized if the compartment is fully filled with CSF.

Of 207 severe eye injuries in a report of military casualties in Operation Iraq Freedom OIF, 82 percent were caused by blast and blast fragmentation. Eye injuries accounted for 13 percent (19/149) of all battlefield injuries seen at a combat support hospital during Operations Desert Shield and Desert Storm Hyphema (blood within the anterior chamber) and traumatic cataract were the most common findings in closed globe injuries, the majority (67%) of eyes sustained orbital injury. Of the service members experiencing combat ocular trauma (COT) in Operation Enduring Freedom, 66 percent also had TBI. Simply stated, roughly two-thirds of the combat related eye injuries were closed blast wave energy absorptions resulting in rupture.

Traumatic brain injury, or the concussive or blast-related events leading to TBI, has also been found to be a leading cause of anosmia (loss or impairment of olfactory function, i.e., sense of smell). Certain studies have reported that a large proportion of patients with post-traumatic anosmia exhibit abnormalities in the olfactory bulbs and in the inferior frontal lobes, suggesting in the latter case that reducing TBI can reduce the risk of anosmia. While loss or impairment of olfactory function can be more than a nuisance to humans, the same injury to Breecher dogs (e.g., bomb sniffers) can be catastrophic. Breecher dogs are inherently exposed to the risk of concussive events and their primary purpose is to help soldiers avoid such an event. Preventing or reducing the likelihood of TBI and associated loss of smell can be critical to the Breecher dog's mission.

Standard prophylactic measures designed to protect the brain against injury in the case of head trauma have hitherto included only various helmets. Helmets are primarily designed to protect the skull from penetrating injuries and fractures, but less so from pathological movements of the brain, exemplified by the classic cerebral concussion. Moreover, helmets have no meaningful effect on blast-related injuries to the ear, spinal column and eyes.

SUMMARY

Intracranial injuries due to exposure to external concussive forces remains a devastating condition for which traditionally extra-cranial protection has been utilized in the form of helmets. Although headgear is effective in preventing the most devastating intracranial injuries, penetrating injuries, and skull fractures, it is limited in its ability to prevent concussions or damage to the structures within the cranium. In accordance with one disclosed method, the internal jugular vein (IJN) is mildly occluded to increase cerebral blood volume and decrease the intracranial compliance. This results in a reduction of the differential acceleration between the skull and its contents, less propensity for brain and fluid movement inside the skull, resulting in less shearing and tearing forces and less energy absorption by the contents, all resulting in less traumatic axonal and glial injury. Compression of the IJV also leads to increased cochlear pressure to mitigate the damage risk to the inner ear, increased pressure in the cerebrospinal fluid to reduce the risk of injury to the spinal column, and increased intraocular pressure to protect the internal structure of the eye from these concussive events.

In an attempt to mitigate intracranial slosh it is recognized that the single intracranial compartment that is most amenable to rapid, reversible change in volume and pressure is the blood space. The simplest and most rapid means of increasing the blood compartment is to inhibit its outflow by mechanically obstructing the draining veins in the neck.

One aspect of the disclosure, therefore, encompasses embodiments of a device to reduce SLOSH energy absorption in an animal or human subject by reducing the flow of one or more neck veins by compressing at least one of said vessels, wherein the device can comprise a collar configured to at least partially encircle the neck of an animal or human subject, and at least one region inwardly directed to contact the neck when encircled by the collar, thereby applying a localized pressure to a neck vein.

In some embodiments of this aspect of the disclosure, the at least one region inwardly directed to contact the neck can be disposed on said collar to exert pressure in the area of an internal jugular vein when the neck of an animal or human subject is inserted in said collar.

In some embodiments of this aspect of the disclosure, the collar can be elastic. In some embodiments of this aspect of the disclosure, the collar size and tension thereof can be adjustable. In some embodiments of this aspect of the disclosure, the device can further comprise one or more breakaway release mechanisms.

In some embodiments of this aspect of the disclosure, at least one region of the device inwardly directed to contact the neck of a subject can be formed by inflation of a region of the collar, and wherein the device optionally further comprises a pump to inflate the inflatable protuberance, or any region of said device, and optionally a source of pressurized gas or fluid for inflation thereof. In some embodiments of this aspect of the disclosure, the device can further comprise a release valve to regulate the pressure in said collar.

Another aspect of the disclosure encompasses embodiments of a method of increasing the intracranial pressure of an animal or human subject comprising: (i) encircling the neck of an animal or human subject with a collar, wherein said collar has at least one region inwardly directed to contact the neck of an animal or human subject; (ii) positioning the at least one region inwardly directed to contact the neck on a region of the neck overlying a neck vein carrying blood from the intracranial cavity of the subject; and (iii) applying pressure to the neck vein by pressing the at least one region inwardly directed to contact the neck onto the surface of the neck, thereby restricting blood flow egressing the intracranial cavity of the subject, thereby increasing the intracranial pressure and or volume of the subject.

Further aspects of the present disclosure provides methods for mitigating injury to the inner ear, ocular structure and the spinal column, and for preventing loss of olfactory function. In the method for mitigating injury to the inner ear, pressure is applied to the jugular veins to thereby increase cochlear fluid pressure during the concussive event. In the method for mitigating injury to the ocular structure, pressure is applied to the jugular veins to thereby increase intraocular fluid pressure during the concussive event. In the method for mitigating injury to the inner ear, pressure is applied to the jugular veins to thereby increase cerebrospinal fluid pressure during the concussive event. Applying pressure to the jugular veins also reduces or prevents loss of olfactory sense due to increased intracranial pressure.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1A:
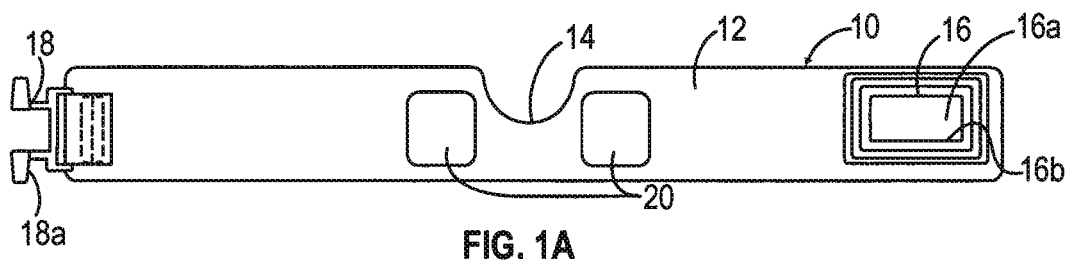
FIGS. 1(a)-1(c) are top and side views of a compression collar according to one disclosed embodiment.

The drawings are described in greater detail in the description and examples below.

DETAILED DESCRIPTION

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

When liquid in a tank or vessel experiences dynamic motion, a variety of wave interactions and liquid phenomena can exist. The oscillation of a fluid caused by external force, termed "sloshing", occurs in moving vessels containing liquid masses, such as trucks, aircraft, and liquid fueled rockets. This sloshing effect can be a severe problem in energy absorption, and thus, vehicle stability and control. The present disclosure encompasses methods and apparatus for reducing SLOSH effects in living creatures, and in particular in the intracranial regions of the animal or human subject.

The mitigation of blast wave and collision damage is based largely on the principle of energy absorption of fluid-filled containers. As there becomes more room for movement of fluid within a vessel, more energy can be absorbed (SLOSH) rather than transmitted through the vessel. To reduce this energy absorption, one must attempt to more closely approximate elastic collisions. Elastic collisions are those that result in no net transfer of energy, chiefly, acoustic, kinetic, vibrational, or thermal (also stated as a coefficient of restitution (r) approximating 1.0). Various embodiments described below may locally alter, elevate, or temporarily maintain an altered physiology of an organism to reduce the likelihood of energy absorption through SLOSH whereby the coefficient of restitution (r) is increased. The coefficient of restitution (r) indicates the variance of an impacting object away from being a complete total elastic collision (an (r) of 1.0=no energy transfer). Blast or energy absorption in an organism can be viewed as a collision of bodies and thus be defined by a transfer of energies through elastic or inelastic collisions. The mechanisms for biological fluids and molecules to absorb energy can thus be identified and the resultant means to mitigate that absorption can be achieved through several SLOSH reducing techniques. Dissipation of energies post blast is also potentiated through these techniques.

SLOSH absorption may also be reduced by reversibly increasing pressure or volume within the organs or cells of the organism. The intracranial volume and pressure can be reversibly increased by a device that reduces the flow of one or more outflow vessels of the cranium of said organism. One embodiment of such a device would compress the outflow vessels enough to cause an increase in venous resistance, yet not surpass arterial pressure of approximately 80 mm Hg. Intracranial volume can also be reversibly increased by increasing the $pCO_2$ in the arterial blood or by the delivery of one or more medicaments to facilitate an increase in intracranial volume or pressure including but not limited to Minocycline, insulin-like growth factor 1, Provera, and Vitamin A.

With respect to the inner ear, it is known that the cochlear aqueduct is in direct communication with the cerebrospinal fluid (CSF) and the vein of the aqueduct drains directly into the internal jugular vein (IJV). The venous blood empties either directly into the inferior petrosal sinus or internal jugular vein, or travels through other venous sinuses via the vein of the vestibular or cochlear aqueduct. Reduced outflow of the internal jugular would necessarily congest the cochlear vein and take up the compliance of the inner ear, thereby improving elastic collisions at the macroscopic, cellular, and molecular level and, thus, reducing energy impartation into these structures.

With respect to protecting the spinal column, increasing CSF volume has generally the same effect as a completely filled cylindrical can versus a partially filled can. Just as a filled can has a greater axial load bearing capacity than an empty can, "filling" the spinal volume can increase the load bearing capacity of the spinal column, thereby preventing blast-related spinal cord injuries. For instance, it is known that an empty cylindrical can is only able to support an axial load for a very short period of time before it buckles. A full can is able to sustain the axial load for a much longer time, as well as support a larger axial load than the empty can. From the perspective of the spinal column, increasing the length of time that the column can sustain an axial load before "collapse" or increasing the axial load that the column can endure will reduce the likelihood of blast-related injuries. Moreover, reducing SLOSH within the spinal tract will reduce the damage to the living tissues within the column (i.e., spinal strands) due to SLOSH.

With respect to ocular injuries, it is known that the woodpecker has a "pectin apparatus" that protects the globe of its eyeball from the 1200 G impact of pecking The sole purpose of the pectin apparatus appears to be to increase the volume and pressure of the vitreous humor inside the eyeball. The pectin apparatus is situated within the eyeball and fills with blood to briefly elevate intraocular pressure, thereby maintaining firm pressure on the lens and retina to prevent damage that might otherwise occur during the 80 million pecking blows over the average woodpecker's lifetime. While humans lack the pectin apparatus it is possible to increase intraocular pressure by application of circumferential pressure on the external jugular veins.

One aspect of the disclosure, therefore, encompasses embodiments of a compression device that when applied to the neck of a subject animal or human to reduce the likelihood of energy absorption to the brain through raising intracranial and intraocular volume and pressure by applying pressure to the outflow vasculature and/or cerebral spinal fluid of the brain. The result would be an increase in the structure's coefficient of restitution (r) by attaching a cinch or collar around the neck of the individual or organism. The compression device can be of any design including, but not limited to, a band or cord. Such a compression device could be worn preferably before, in anticipation of and during events with SLOSH and traumatic brain injury risks. The compression device of the disclosure further includes at least one protuberance or thickened region of the device that may be positioned over an underlying neck vein to apply a localized pressure thereto.

Safely and reversibly increasing cerebral blood volume by any amount up to 10 cm·sup·3 and pressure by any amount up to 70 mmHg would serve to fill up the compliance of the cerebral vascular tree and thus reduce the ability to absorb external energies through SLOSH energy absorption. With the application of measured pressure to the neck, the cranial blood volume increases rapidly and plateaus at a new higher level. Moyer et al reported that cerebral arterial blood flow was not affected by obstructing the venous outflow of blood from the brain. The blood volume venous pressure relationship shows a diminishing increase in volume with each increment of neck pressure over the range 40 to 70 mm of mercury. It is of interest that the cranial blood volume increases from 10 to 30 percent (with this neck pressure). The cerebral spinal fluid pressure responds on compression of the individual jugular veins. The average rise was 48 percent. Jugular compression increases cerebral blood flow to a new plateau in as little as 0.5 seconds. This degree of cranial blood volume and pressure increase would be very beneficial in SLOSH mitigation. Although lesser cranial pressure and volume increases may still have beneficial effects, an increase of 3 cm$^3$ volume and 5 mm Hg is a baseline goal. However, if pressure is distributed along the length of the veins, much less pressure, for example, as little as 5-10 mmHg is sufficient to increase flow resistance in the veins.

Further, safety of such a procedure of venous compression is quite abundant in the literature as it mirrors the 100 year old Quenkenstadt Maneuver. In this maneuver, the compression of the neck does not interfere with arterial flow into the cranium. Although the venous jugular flow beneath the pressure cuff may be temporarily halted, the venous outflow from the cranium is never completely stopped, particularly from the anastomosis between the spinal vein and the basilar plexus and occipital sinuses which are incompressible. In fact, there was no correlation between Electroencephalographic (EEG) changes or changes in systolic arterial blood pressure occurring during jugular compression. Thus, neck compression of up to 70 mmHg does not affect cardiac output, arteriolar blood pressure, pulse rate, or urine flow.

Embodiments of the collar of the disclosure, therefore, comprise a collar that can encircle completely or partially the neck of a subject animal or human, and is sized such that the collar can apply an external pressure over the regions of the neck overlying the internal jugular veins. It is contemplated that this pressure may be due to the internal dimension of the collar being less than the neck diameter resulting from the size of the collar or the elasticity thereof, or the result of decreasing the internal diameter of the collar by any method such as inflating the collar, a region thereof, or of at least one protuberance thereof. The external pressure applied to the internal jugular vein will result in a restriction of blood flow through the vein.

In particular, the collar of the device according to the disclosure, therefore, includes at least one protuberance, stud, thickened or expandable region directed inwardly and disposed on the surface of the collar that is proximal to the skin when applied to a neck so as to be positioned directly over a region of a neck vein. It is contemplated that the at least one protuberance, stud, thickened or expandable region can be a fixed protuberance or stud resistant to deformation when applying pressure to a neck, or may be enlarged by inflation of an inflation device connected thereto. An inflatable protuberance may be positioned over a neck vein and then inflated to apply pressure to the underlying blood vessel. In the alternative, the at least one protuberance may be non-inflatable but disposed on an inflatable collar.

It is further contemplated that the collar of the disclosure and/or inflatable protuberance(s) disposed thereon may be operably connected to an inflation means such as, but not limited to, a powered pump, or a hand-compressible pump whereby a liquid, air or a gas can be applied to the collar. In certain embodiments the collar may further comprise a pressure sensor operably linked to the inflation means whereby the degree of inflation of the collar and/or protuberance(s) thereof may be regulated as to the extent and duration of the pressure applied to an underlying neck vein.

It is also contemplated that the protuberance(s) of the collar of the disclosure may be configured to apply pressure to an area approximately the diameter of an internal jugular vein, greater than said diameter, and may be of any shape that can provide partial restriction of the blood flow through the neck vein, including a pointed protuberance, a stud, a thickened region of the collar, and the like.

The compression device may be of any material including, but not limited to, elastic materials, or more particularly materials that are elastically elongatable around the circumference of the subject's neck. Elastic materials can be any material which when stretched will attempt to return to the natural state and can include one or more of textiles, films (wovens, non-wovens and nettings), foams and rubber (synthetics and natural), polychloroprene (e.g. NEOPRENE®), elastane and other polyurethane-polyurea copolymerss (e.g. SPANDEX®, LYCRA®), fleece, warp knits or narrow elastic fabrics, raschel, tricot, milanese knits, satin, twill, nylon, cotton tweed, yarns, rayon, polyester, leather, canvas, polyurethane, rubberized materials, elastomers, and vinyl. There are also a number of elastic materials which are breathable or moisture wicking which may be preferable during extended wearing periods or wearing during periods of exercise. In addition, the compression device could be partially constructed, coated, or constructed of one or more protecting materials such as Kevlar (para-aramid synthetic fibers), Dyneema (ultra-high-molecular-weight polyethylene), ceramics, or shear thickening fluids.

The device may encompass circumferentially, the entire neck or just partially around the neck, yet still providing partial or total occlusion of one or more of the outflow vessels on the neck, specifically, but not limited to the internal and external jugular veins, the vertebral veins, and the cerebral spinal circulation. The device may encompass horizontally, the entire neck or just partially up and down the neck.

The width of the compression device may range from a mere thread (at a fraction of an inch) to the length of the exposed neck (up to 12 inches in humans or greater in other creatures), the length may range from 6 to 36 inches to circumnavigate the neck. The width of the compression device could be as small as ¼ inch but limited only by the height of the neck in largest width, which would be typically less than 6 inches. The thickness of said device could range from a film being only a fraction of a millimeter to a maximum of that which might be cumbersome yet keeps one's neck warm such as 2-3 inches.

One embodiment of the compression device may be preformed for the user in a circular construct. This one size fits all style can have a cinch of sorts that allows one to conform the device to any neck size. Alternatively, the compression device may have a first end and a second end which are connected by a fastener. A fastener may be a hook and ladder attachment, a hook and loop attachment, a snap, a button or any of a number of attachment mechanisms that would be known to one skilled in the art. A compression device with a fastener could have a breakaway release mechanism whereby the device can break open or apart at a predetermined force to prevent the collar from inadvertently being snagged or compressing too tightly. One quick release or automatic release embodiment would be the applying of small amounts of hook and ladder attachments within the circumferential ring which would shear apart upon too much force being applied to the compression device. Another embodiment of the device could fasten such that the user would be able to pull one end of the collar (like a choker collar for a dog) and the force exerted by the user effectually decreases the length or circumference of the device. When the desired neck compression is no longer needed (such as between football plays) the user could then release the compression by a second gentle tug or by a separate release mechanism also positioned on the device.

In yet another embodiment of the collar device of the disclosure, the protuberances that can apply a compressive pressure to an internal jugular vein are compressible pads or solid forms sized to apply pressure substantially only to internal jugular vein. It is contemplated that at least one pad or rigid form may be connected to one or both opposing ends of a resilient arcuate connector that conforms to a predetermined configuration such that the opposing ends of the connector may be displaced to allow the pad(s) or rigid form(s) thereon to be disposed on the neck to apply pressure to the underlying internal jugular vein.

The compression device may have one or more protuberances, or otherwise not be of consistent thickness or width. One such embodiment may have thicker protruding regions to be aligned with the internal jugular veins to preferentially apply a compressive pressure to these veins as the collar is tightened. Another embodiment may utilize inflatable protuberances as further described below.

The compression device may also have one or more monitoring, recording, and/or communicating devices attached or embedded. One such embodiment of the invention would be to embed a transceiver and/or receiver to allow communications between soldiers on a battlefield or even between coaches and players. Further, cardiac monitors could include heart rate or plethysmography monitors that could provide real time evaluation of cardiophysiology while the compression device is in place.

The compression device can also have a pocket or pouch attached depending on the height of the compression device used. Certainly, advertising can be imprinted or emblazoned onto the device. One such embodiment of the invention would have a wider segment of the collar positioned at the back of the neck on which to print a commercial design or brand name.

One other means of restricting blood flow within the neck vasculature would be to incorporate one or more segments of inflatable bladders within the collar to alter the circumference or pressure the collar is exerting. One such embodiment could utilize a bulb pump placed in connection to the bladders whereby the user would compress the bulb one or multiple times until the desired pressure of air or fluid is retained within the bladder of the collar. Another embodiment may utilize pressurized gas or fluid which is connected to the bladders. Another embodiment would have a pressure release valve in communication with the bladders such that once a predetermined pressure is reached within the bladder, any successive pumping actions would merely divert the air or fluid pressure to the ambient air or the pump itself would simply no longer inflate (an existing correlate example would be the historical "Reebok Pump"). An embodiment with a pressure release valve could prevent over inflation of bladders and allow for a very precise degree of pressure delivery to the vasculature.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

In some embodiments of this aspect of the disclosure, the device can further comprise a plurality of compressible pads or rigid forms sized for applying pressure substantially only to a internal jugular vein, wherein at least one pad or form is disposed at each opposing end of the resilient arcuate connector.

Figure 1B:
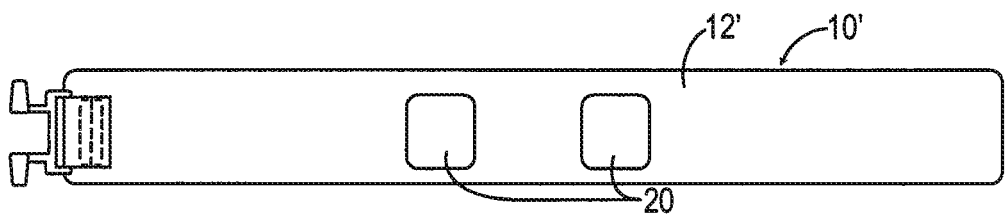
Figure 1C:
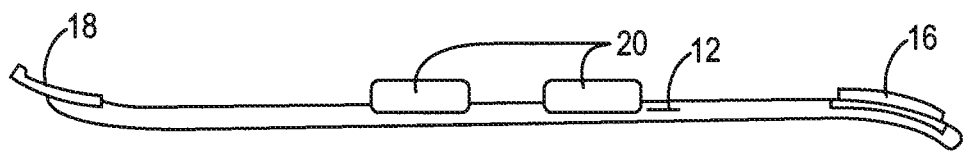
Figure 2:
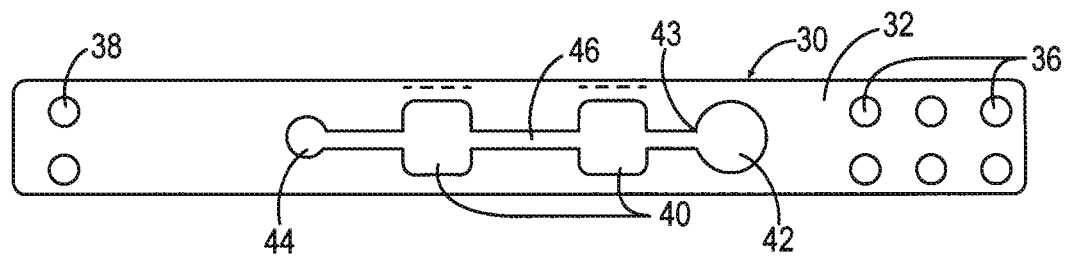
FIG. 2 is a top view of a compression collar according to a further disclosed embodiment.
Figure 3:
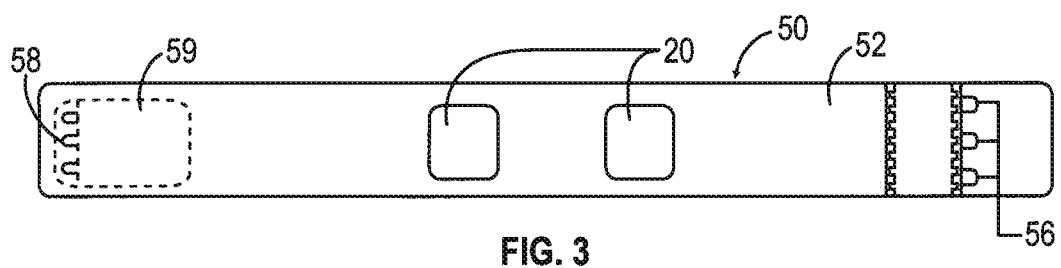
FIG. 3 is a top view of compression collar according to another disclosed embodiment.

Particular embodiments of the collar are illustrated in FIGS. 1-3. Referring to FIGS. 1(a)-(c), a compression collar 10 includes an elongated strap 12 that may be provided in various sizes to encircle the neck of the animal or human subject. In one specific embodiment the strap may be provided in standard lengths of 14, 16 and 18 inches to fit the normal range of neck sizes for humans. The width in a specific example may be about 1.5 inches to fit within the anatomy of the neck below the laryngeal prominence. To minimize the prominence of the collar, the strap may have a thickness of about 0.12 inches. The strap 12 may be formed of a woven, breathable, dermatologically inert and non-irritating material, such as cotton or certain polyesters. Since the strap is intended to apply consistent pressure to the jugular vein of the subject the strap material is preferably generally elastic, but formed of an elastic material that will not permanently stretch appreciably over time. It can be appreciated that stretching the material so that the neutral length of the strap is longer than its original condition can render the strap 12 useless. On the other hand, the strap material must be sufficiently elastic or elastically elongatable to remain comfortable when worn for a long period of time, and to flex appropriately with the muscles of the neck. The effective length of the strap 12 is made adjustable by the addition of adjustable engagement elements 16 and 18 at opposite ends of the strap. For instance, in the embodiment shown in FIG. 1(a) the latch element 16 defines a serrated channel 16a that receives the resilient prongs 18a of the other element. The prongs 18a are biased to provide an outward force against the channel 16a of the latch to hold the prongs at the location of a particular serration 16b. In the illustrated embodiment, seven serrations are depicted which provide seven locations for engagement of the prongs 18a for fine adjustment of the length of the collar. The two components 16, 18 may be sewn onto the strap 12 or permanently affixed in a conventional manner sufficient so that the engagement elements will not pull free from the strap during use.

Two versions of the collar are depicted in FIGS. 1(a) and 1(b). The version of FIG. 1(a) is provided for a male human and includes a cut-out 14 at the location of the laryngeal prominence. The strap 12' of FIG. 1(b) does not include the cut-out and may be typically provided for female human subjects. The cut-out may have a width of about 1.5 inches and a depth of about 0.5 inches to accommodate the typical laryngeal prominence. It can be appreciated that the collar 10 is engaged around the neck of the subject so that the cut-out 14 is below and sufficiently clear of the prominence to avoid any discomfort to the subject.

In a further feature of the collars 10, 10', a pair of compressible pads 20 are provided spaced apart across the midline of the strap 12, 12'. The pads are sized and located to bear against the neck at the location of the jugular veins. In one embodiment the pads are spaced apart by about 2.5 inches, have a width/length dimension of 1.0-1.5 inches and a thickness of about 0.04 inches. As shown in FIG. 1(c) the pads may be partially embedded within the strap 12. The pads 20 may be formed of a breathable foam that exhibits good recovery from compression. The pads may be formed of a material capable of exerting compression of 5-30 mm Hg when the collar is worn, such as a flexible polyurethane foam.

Additional embodiments of the compression collar are shown in FIGS. 2 and 3 that incorporate different engagement elements. For instance, the collar 30 of FIG. 2 incorporates an array of snap pairs 36 at one end that engage a pair of snaps 38 at the opposite end. The snap pairs 36 may be spaced at pre-determined intervals, such as at ¼ inch spacings to permit adjustment of the collar diameter when worn. The collar 50 in FIG. 3 incorporates a row of hooks 56 at one end that engage a corresponding row of loops 58 at the opposite end. The embodiment of FIG. 3 illustrates that the engagement elements need not be adjustable, although adjustability is preferred. In the embodiment of FIG. 3 this adjustability may be accomplished by a VEL-CRO® type connection between the strap 52 and the row of loops 58. In particular, a VELCRO® type pad interface 59 may be used to mount the loops 58 to the strap at different positions along the length of the strap. In a further alternative, the VELCRO® interface may be between the two ends with mating VELCRO® type pads on each end.

In one aspect of the compression collars disclosed herein, the engagement elements are preferably configured to break loose or disconnect at a certain load, to avoid the risk of choking or damaging the subject's neck and throat if the collar is snagged or grabbed. Thus, the engagement elements 16, 18 of FIG. 1, the snaps 36, 38 of FIG. 2 and the hook attachment 59 of FIG. 3 can be calibrated to disconnect when the collar is pulled with sufficient force. In a further embodiment, the engagement elements, such as snaps 36, 38, may be replaced by magnets or a magnet array. The magnets are strong enough to maintain the desired pressure on the jugular veins when the collar is in use. The magnet strength may be calibrated to break loose at a certain load. The break-away feature may also be integrated into the strap apart from the engagement elements. For instance, the strap may incorporate a region between a pad 20 and an engagement element that has a reduced strength so that the strap tears under a certain load. Alternatively, a non-adjustable engagement may be provided in this region calibrated to disengage at a predetermined load.

In the embodiments of FIGS. 1 and 3, the jugular vein is compressed by the pad 20. The pad has a predetermined thickness and compressibility. In an alternative embodiment, the pads are replaced by inflatable bladders 40, as shown in FIG. 2. In this embodiment a fluid line 46 connects the bladders to a pump 42 and a release valve 44. The pump 42 can be of the type that is manually squeezed to draw atmospheric air into the bladders. A one-way valve 43 is provided in the fluid line 46 at the pump 42 to maintain the increasing air pressure within the bladders. The pump 42 may be constructed similar to a small engine primer bulb. The pump may be configured to be manually depressed while the collar is being worn. The release valve 44 may be manually activated to relieve the bladder pressure. The release valve may also be configured to automatically vent when a certain pressure is reached to prevent over-inflating the bladders 40.

In an alternative embodiment the pump 42 may be a microfluidic pump embedded within the strap 32. The pump may be electrically powered by a battery mounted within the collar or may be remotely powered such as by an RF transmitter placed adjacent the collar. The pump may be remotely controlled by incorporating a transmitter/receiver within the collar. The receiver may transmit pressure data indicating the fluid pressure in the bladders 40 and the receiver can receive remotely generated commands to activate the pump 42 to increase the pressure to an appropriate value. It is further contemplated that the pump 42, whether manually or electrically operated, may include a pressure gage that is readable on the outside of the collar to assist in inflating the bladders to the desired pressure.

The illustrated embodiments contemplate a collar that completely encircles the neck of the subject. Alternatively, the compression device may only partially encircle the neck. In this embodiment the device may be a resilient arcuate band having a general C-shape. The band may be formed of a resilient spring-like material with the compression pads mounted to the ends of the C-shape. The device would thus function like a spring clip to exert pressure against the jugular vein. The spring effect of the C-shape can also help hold the device on the subject's neck, preferably on the back of the neck for better anatomic purchase.

Figure 4:
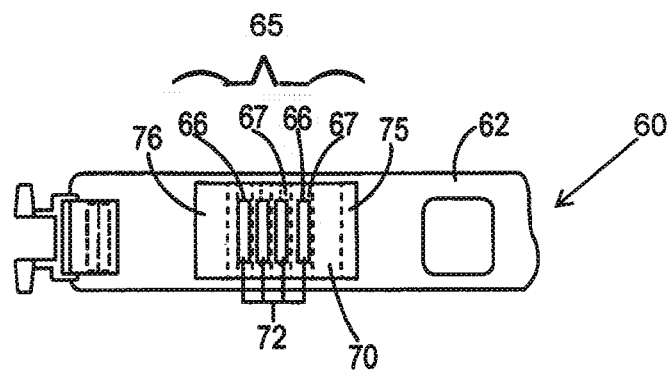
FIG. 4 is a top view of a compression collar of another embodiment incorporating a compression indicator.
Figure 5:
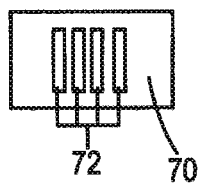
FIG. 5 is a top view of an overlay to be mounted on the collar of FIG. 4.

A compression collar 60, shown in FIG. 4, may incorporate a visual compression indicator that can be visualized when the collar is fitted on a user. The collar 60 includes a strap 62 that may be configured like the straps 12, 32, 52 described above, and may incorporate compression pads 20, 40 arranged to apply pressure to the jugular vein when the strap encircles the neck of the subject. The strap 62 is elastic so that the strap must be elongated or stretched when worn to apply the desired pressure to the IJV. The strap 62 includes an array 65 of stripes 66, 67 of alternating colors. For example, the stripes 66 may be red (to signify a no-go condition) while the stripes 67 may be green (to signify a go condition). The compression collar 60 further includes an overlay 70, shown in FIG. 5, which includes a number of windows 72. The stripes 66, 67 and windows 72 are in like numbers (four in the illustrated embodiment), have the same width and are spaced apart the same dimension. In one specific embodiment the stripes 66, 67 have a width of 2 mm, while the windows 72 have a width of 2 mm and are spaced apart by 2 mm.

Figure 6:
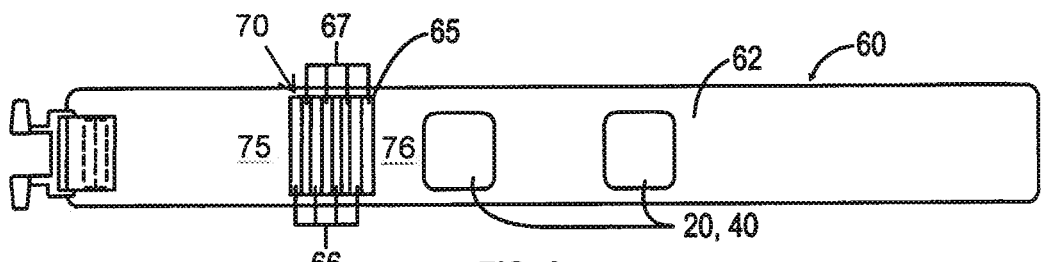
FIG. 6 is a top partial view of the compression collar and overlay of FIGS. 4-5.
Figure 7A:
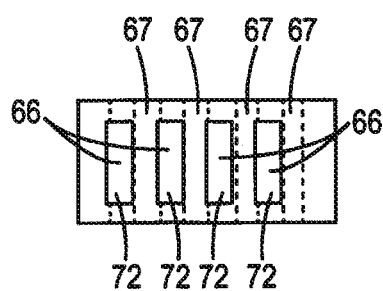
FIGS. 7(a)-7(c) are successive views of the overlay and indicator strips of the compression collar shown in different degrees of stretch of the collar.
Figure 7B:
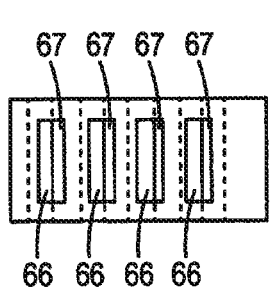
Figure 7C:
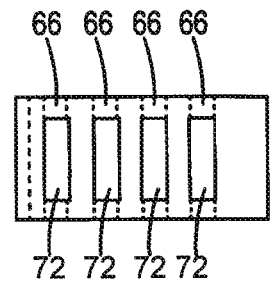

As shown in FIG. 6, the overlay 70 is fastened at one end 75 to the strap 62. The opposite end 76 is not fastened to the strap to thereby permit the strap to stretch beneath the overlay. In the embodiments described above the entire strap is elastically elongatable. For the compression indicator at least the portion of the strap in the region of the overlay 70 must be elastic and able to elongate or stretch relative to the overlay. The overlay 70 is affixed to the strap 62 so that all or a substantial portion of the "no-go" stripes 66 are visible in the windows 72 when the strap is in its neutral, unstretched configuration (i.e., before the collar is fitted to the subject), as shown in FIG. 7(a). When the collar is fastened around the subject's neck it will stretch and as it stretches the stripes 66, 67 advance relative to the windows 72 of the overlay 70. Thus, as shown in FIG. 7(b), a portion of both stripes 66, 67 will be visible through the windows. When the strap is stretched a predetermined amount to apply the desired pressure to the IJV, the "go" stripes 67 will be fully or substantially visible in each window 72, as shown in FIG. 7(c). If the strap is stretched too much, the "no-go" stripes 66 will again be visible in the windows. The compression indicator achieved by the stripe array 65 and overlay 70 thus provides a direct visual indicator as to whether the collar is applying the desired amount of pressure to the IJV. The collar may be adjusted so that the "go" stripes 67 are visible by adjusting the engagement elements, or by using a collar having a different starting length. For instance, for the collar 30 of FIG. 2, a different row of snaps 36 may be mated to the snaps 38 to achieve the desired compression.

In the embodiment of FIGS. 4-7, the array 65 includes four sets of parallel stripe pairs 66, 67. However, other visual indicia in any number of pairs may be utilized with appropriate modifications to the windows 72 of the overlay. For instance, array 65 may include visual indicia "GO" and "NOGO" or other words suitable to convey when the collar 60 is applying an appropriate amount of pressure to the IJV. Alternatively, the array may include a single indicia that is visible through a single window in the overlay when the collar is properly adjusted around the neck of the subject. The compression indicator is preferably oriented on the collar at a location that is visible to the subject when looking at a reflective surface. Alternatively, the indicia on the strap 62 may be a tactile indicator that can be felt by the subject's finger through the window(s) in the overlay.

Another aspect of the disclosure encompasses embodiments of a method of increasing the intracranial pressure of an animal or human subject comprising: (i) encircling the neck of an animal or human subject with a collar, wherein said collar has at least one region inwardly directed to contact the neck of an animal or human subject; (ii) positioning the at least one region inwardly directed to contact the neck on a region of the neck overlying a neck vein carrying blood from the intracranial cavity of the subject; and (iii) applying pressure to the neck vein by pressing the at least one region against the neck. In certain embodiments, this compression can be as much as 25 mm Hg without any side effects and without impacting the carotid artery. It is believed that pressures as high as 80 mm Hg can be applied without endangering the jugular vein. For many applications of the method, the pressure applied to the neck vein, or jugular vein, can be 3-15 mm Hg. Applying pressure to the jugular vein can increase ICP up to 30% above the baseline pressure to protect the intracranial cavity from blast-related SLOSH effects without any side effects.

In accordance with one embodiment of the method, a compression collar, such as the collars 10, 10', 30 and 50 are placed low on the neck of the subject and more particularly between the collar bone and the cricoids cartilage or laryngeal prominence. This location is distant from the carotid sinus which is higher on the neck, so application of pressure to the neck will not compress the carotid artery. In the case of a male subject, the cut-out 14 of the strap 12 is positioned directly beneath the laryngeal prominence.

The collar may be pre-sized to the subject so that it automatically delivers the proper amount of compression when the ends of the collar are connected. Moreover, as explained above, the engagement elements (i.e., the latching elements 16, 18, the snaps 36, 38, the hooks 56, 58 or the VELCRO® connection) may be configured to break away or disengage if the pressure exceeds a desired value. This break away feature may also be applied with the pump embodiment of FIG. 2 in which case the bladders 40 can be inflated until the elements become disengaged, at which point the valve 44 may be actuated to bleed off some pressure from the bladders prior to refitting the collar on the subject's neck. In the alternative embodiment of the pump discussed above in which the pump is provided with a pressure gage, the bladders are inflated to the desired pressure indicated on the gage. In most cases, the desired compression provided by the collar may be in the range of 15-20 mm Hg, although higher pressures are well tolerated and may be indicated for certain subjects.

It can be appreciated that the collar is only worn when the subject may be exposed to a concussive event, such as a blast during a military battle or hard contact during a sporting activity. Once exposure to such an event ceases the collar may be removed.

Example 1

Materials and Methods: Two groups of ten (total of 20) male Sprague-Dawley rats weighing between 350 and 400 grams were used. Animals were housed under 12 hour light/12 hour dark conditions with rat chow and water available ad libitum.

Marmarou impact acceleration injury model in rats: Anesthesia was induced and maintained with isoflurane using a modified medical anesthesia machine. Body temperature was controlled during the approximately 10 min. procedures using a homeothermic heating blanket with rectal probe, and adequate sedation was confirmed by evaluation of response to heel tendon pinch. The animals were shaved and prepared in sterile fashion for surgery, followed by subcutaneous injection of 1% lidocaine local anesthetic into the planned incision site. A 3 cm midline incision in the scalp was made and periosteal membranes separated, exposing bregma and lambda. A metal disk 10 mm in diameter and 3 mm thick was attached to the skull with cyanoacrylate and centered between bregma and lambda.

The animal was placed prone on a foam bed with the metal disk directly under a Plexiglas tube. A 450-g brass weight was dropped a single time through the tube from a height of 2 meters, striking the disk. The animal was then ventilated on 100% oxygen while the skull was inspected, the disk removed, and the incision repaired. When the animal recovered spontaneous respirations, anesthesia was discontinued, and the animal was returned to its cage for post-operative observation. Buprenorphine was used for post-operative analgesia.

Example 2

Experimental protocol: This work involved two groups, each consisting of 10 animals for a total of 20 animals. Two groups were utilized, a control injury group and an experimental injury group. In the experimental injury group, the rats were fitted with a 15 mm wide collar, with two compressive beads designed to overlay the IJVs and was tightened sufficiently to provide mild compression of the veins without compromising the airway. The collar was then fixed in circumference with a Velcro fastener. The collar was left in position for three minutes prior to administrating experimental brain injury.

Assessment of Intracranial Reserve Volume Intracranial Pressure (ICP) Measurement: ICP was measured in five animals using the FOP-MW pressure sensor (FISO Technologies, Quebec, Canada) as described by Chavko, et al. The head of the rat was shaved and prepped in sterile fashion for surgery. The rat was fixed in a stereotaxic apparatus (model962; Dual Ultra Precise Small Animal Stereotaxic Instrument, Kopf Instruments, Germany) and a 3 cm midline incision in the scalp was made. Periosteal membranes were separated, exposing both bregma and lambda. A 2 mm burr hole was drilled 0.9 mm caudal from bregma and 1.5 mm from the midline. The fiber optic probe was then inserted to a depth of 3 mm into the cerebral parenchyma.

Intraocular Pressure (IOP) Measurement: IOP was measured in all animals using the TonoLab rebound tonometer (Colonial Medical Supply, Franconia, N.H.) as described in the literature. IOP measurements were taken after induction of anesthesia in all animals and a second time in the experimental group following application of the IJV compression device. Following application of the IJV compression device in the experimental injury group, IOP readings were taken every 30 secs while the compression device was in place.

Tissue Preparation and Immunhistochemical Labeling: At 7 days post-injury all animals (n=20) were anesthetized and immediately perfused transcardially with 200 ml cold 0.9% saline to wash out all blood. This was followed by 4% paraformaldehyde infusion in Millings buffer for 40 mins. The entire brain, brainstem, and rostral spinal cord were removed and immediately placed in 4% paraformaldehyde for 24 hours. Following 24 hours fixation, the brain was blocked by cutting the brainstem above the pons, cutting the cerebellar peduncles, and then making sagittal cuts lateral to the pyramids. The resulting tissue, containing the corticospinal tracts and the mediallenmisci, areas shown previously to yield traumatically injured axons, was then sagitally cut on a vibratome into 50 micron thick sections.

The tissue underwent temperature controlled microwave antigen retrieval using previously described techniques. The tissue was pre-incubated in a solution containing 10% normal serum and 0.2% Triton X in PBS for 40 mins. For amyloid precursor protein (APP) labeling, the tissue was incubated in polyclonal antibody raised in rabbit against beta APP (#51-2700, Zymed, Inc., San Francisco, CA) at a dilution of 1:200 in 1% NGS in PBS overnight. Following incubation in primary antibody, the tissue was washed 3 times in 1% NGS in PBS, then incubated in a secondary anti-rabbit IgG antibody conjugated with Alexa 488 fluorophore (Molecular Probes, Eugene, OR), diluted at 1:200 for two hours. The tissue underwent a final wash in 0.1M phosphate buffer, and then was mounted using an antifade agent and cover-slipped. The slides were sealed with acrylic and stored in the dark in a laboratory refrigerator.

Fluorescent Microscopy and Image analysis: The tissue was examined, and images acquired using an Olympus AX70 fluorescence microscope system (Olympus; Tokyo, Japan). Ten digital images were obtained from the tissue of each animal and images were then randomized. Individual injured axons were independently counted, and data was stored in a spreadsheet (Microsoft Corp., Redmond, WA). Differences between group means were determined using paired t-tests and considered significant if the probability value was less than 0.05.

Stereological Quantification of axonal injury: A stereo logical method was used to determine an unbiased estimate of the number of APP positive axons per cubic mm in the corticospinal tract and medial lemniscus. The optical fractionator technique utilizing a Stereoinvestigator 9.0 (MBF Bioscience, Inc., Williston, VT) and an Olympus AX70 microscope with 4× and 40× objectives was performed. Sagittal APP stained specimens were examined with low magnification and regions of interest were drawn incorporating the corticospinal tract and medial lemniscus. The software then selected random 50 micron counting frames with depth of 15 microns, and APP positive axons were marked. The volume of the region of interest (ROI) was determined using the Cavalieri method, the volume of the sum of the counting frames was calculated, the sum total of injured axons within the counting frames was calculated, and an estimate of the number of APP positive axons per cubic mm was calculated.

Example 3

Figure 8:
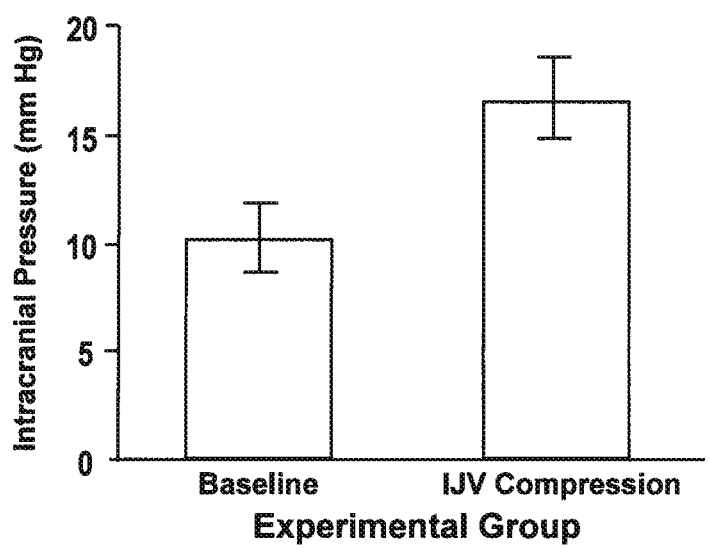
FIG. 8 is a graph illustrating the change in intracranial pressure (ICP) as a consequence of IJV compression, p-value<0.01.
Figure 9:
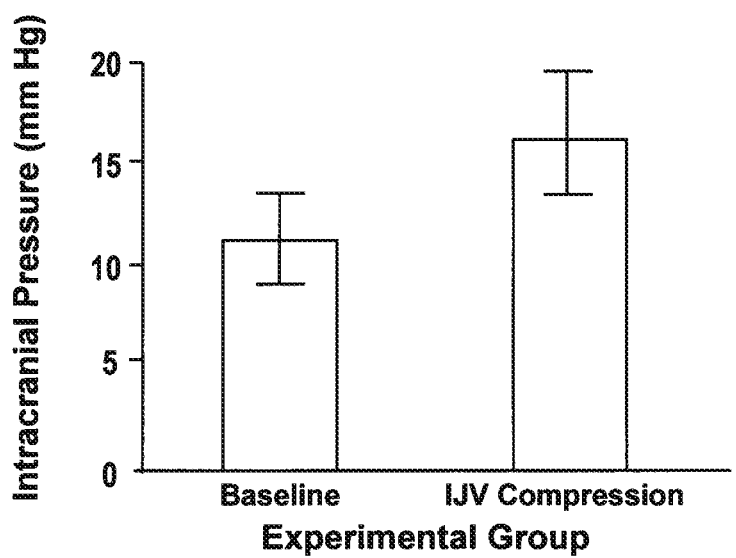
FIG. 9 is a graph illustrating the change in intraocular pressure (IOP) as a consequence of IJV compression, p-value 0.01.

Volume Intracranial Pressure (ICP) Measurement: ICP was assessed both prior to and after application of the IJV compression device. The baseline ICP was 10.23±1.68 mm Hg and was increased to 16.63±2.00 mm Hg following IJV compression (FIG. 8: $p<0.01$). Notably, this increase of greater than 30% from baseline occurred within seconds following IJV compression. Intraocular Pressure (IOP) Measurement: IOP measurements were taken both before and after application of the IJV compression device, similar to ICP recordings. The baseline IOP was 11.18±2.27 mm Hg and was elevated to 16.27±3.20 mm Hg following IJV compression (FIG. 9: $p<0.01$).

Figure 10:
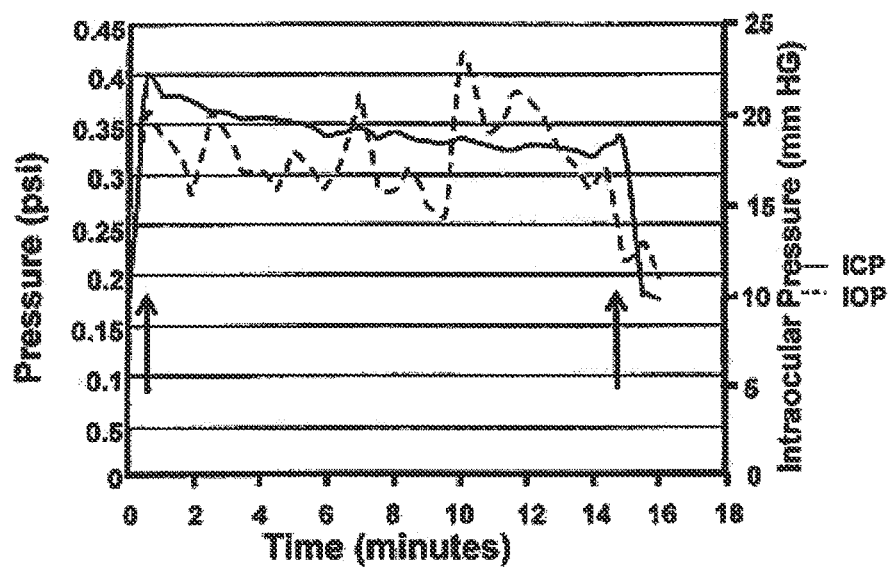
FIG. 10 is a graph showing a representative tracing of physiologic change seen in intracranial pressure (ICP) and intraocular pressure (IOP) over a fifteen minute period caused by the application (arrow on left) and removal of IJV compression (arrow on right). Of note is the rapid response seen in both IP and IOP following IJV compression as well as the duration for which these changes are sustained.

The increase of 31% seen in IOP following IJV compression is strikingly similar to that seen in ICP following IJV compression, both in magnitude and rapidity of response (FIG. 10).

TBI-Impact Acceleration Model: None of the animals died from the head trauma. Animals tolerated collar application without any observed untoward effects for the duration of the experiment. Specifically, there were no outward or visible signs of discomfort, intolerance, or respiratory difficulty. All recovered without complication and exhibited normal behavioral and feeding habits up until the day of sacrifice. At necropsy, the brains were grossly normal in appearance.

Figure 11A:
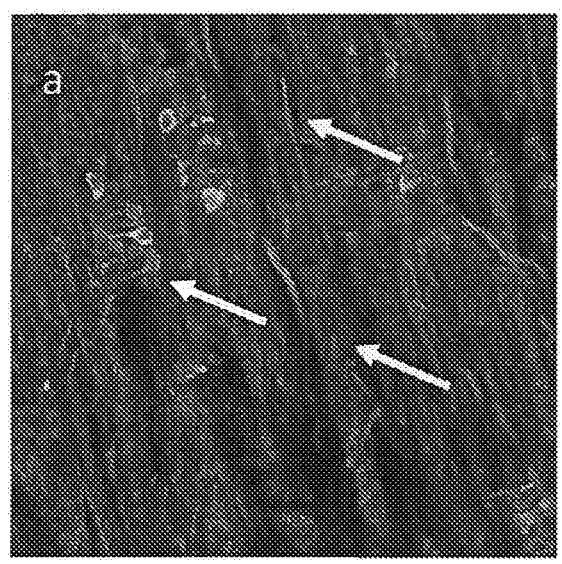
FIG. 11A is a digital image of corticospinal tracts stained for APP post-injury without application of the IJV compression device according to the disclosure.
Figure 11B:
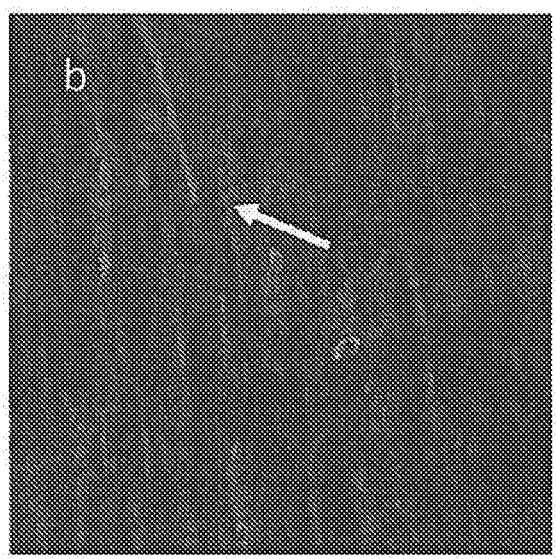
FIG. 11B is a digital image of corticospinal tracts stained for APP post-injury with application of the IJV compression device according to the disclosure.
Figure 12:
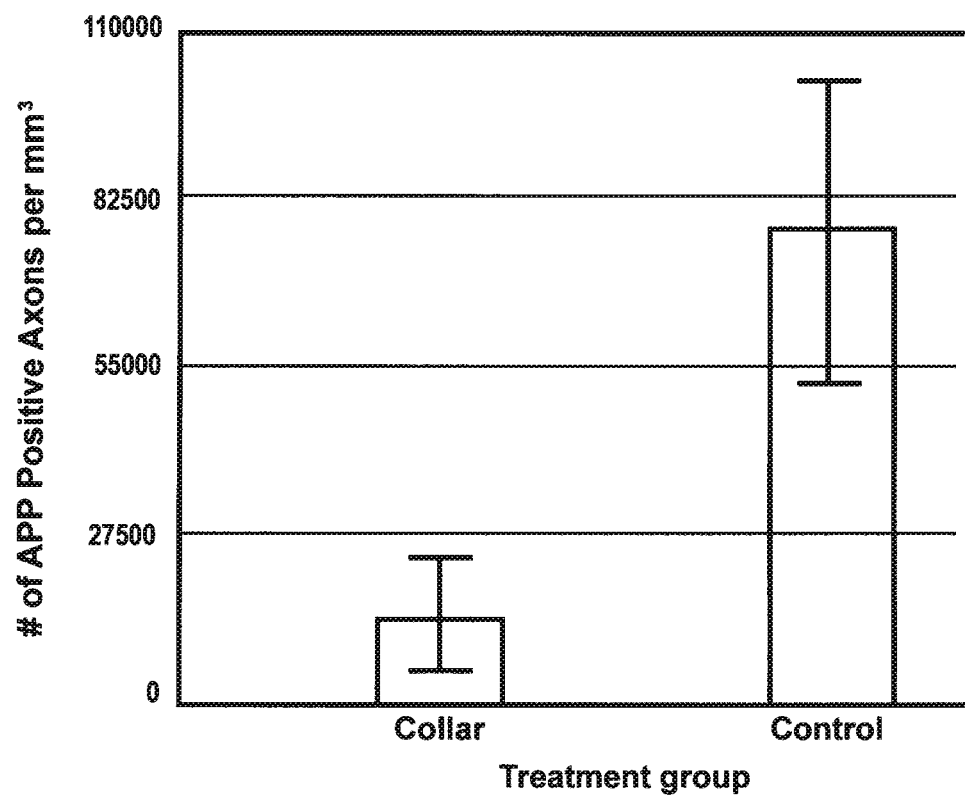
FIG. 12 is a graph illustrating the effect of IJV compression on axonal injury as indicated by APP staining, p-value<001.

Stereologic Analysis of APP Positive Axons: To determine the density of injured axons in the corticospinal tracts and medial lenmisci, the stereo logical optical fractionator method was used. Compared to the normal anatomy found in previous experiments with sham animals, control animals without the collar demonstrated focal labeling of APP within many swollen contiguous and terminal axon segments, consistent with impaired axoplasmic transport in traumatic axonal injury. Following microscopic digital image acquisition from multiple areas within the corticospinal tract and medial lenmisci from multiple tissue slices, counting of APP positive axons in animals who received the IJV compression collar demonstrated much fewer APP positive axons, at a frequency much more similar to sham animals, compared to those undergoing injury without IJV compression (FIGS. 11A and 11B). These abnormal axons demonstrated typical morphological characteristics of traumatic injury, primarily swelling and disconnection. By qualitative analysis, the experimental group showed (m±sd) 13,540±9808 vs. 77,474±25,325 (p<0.01) APP positive axons/mm·sup·3 in the control group (FIG. 12).

Example 4

Two groups of 10 adult male Sprague-Dawley rats were subjected to an impact acceleration traumatic brain injury. Prior to the injury, the experimental group had application of a 15 mm wide cervical collar, which had two compressive beads over the internal jugular veins (IJVs). The control group had the experimental injury only. Intracranial pressure (ICP) and intraocular pressure (IOP) were measured before and after IJV compression to assess collar performance. All rats were sacrificed after a 7-day recovery period, and brainstem white matter tracts underwent fluorescent immunohistochemical processing and labeling of beta amyloid precursor protein (APP), a marker of axonal injury. Digital imaging and statistical analyses were used to determine if IJV compression resulted in a diminished number of injured axons.

Example 5

All animals survived the experimental paradigm and there were no adverse reactions noted following application of the collar. In the experimental group, IJV compression resulted in an immediate and reversible elevation of ICP and IOP, by approximately 30%, demonstrating physiologic changes secondary to collar application. Most notably, quantitative analysis showed 13,540 APP positive axons in the experimental group versus 77,474 in the control group (p<0.0), a marked reduction of greater than 80%.

Using a standard acceleration-deceleration impact laboratory model of mild TBI, a reduction of axonal injury following IJV compression as indicated by immunohistochemical staining of APP was shown. IJV compression reduces SLOSH-mediated brain injury by increasing intracranial blood volume and reducing the compliance and potential for brain movement within the confines of the skull.

Example 6

Internal versus External Brain Protection: Compression of the IJV for 3 min prior to head trauma led to physiological alterations in intracranial compliance, as evidenced by modest increases in ICP and IOP, while simultaneously and markedly reducing the pathologic index of primary neuronal injury in the standardized rat model of TBI. Reduction in brain volume compliance could prevent the differential motions between the cranium and the brain that lead to energy absorption and neuronal primary and secondary injuries. These pathological changes include axonal tearing that disrupt axoplasmic transport resulting in axonal swelling and activation of the apoptotic cascades, as evidenced in this model by a statistically significant reduction in APP counts of injured axons.

In the animal model of the present disclosure, applying the collar increased ICP and IOP by 30% and 31%, respectively. The effect of compression of jugular veins on ICP is clinically well known. The Queckenstadt test is used to indicate the continuity of CSF between the skull and spinal cord. In this test, ICP is increased by compression of the IJVs while the CSF pressure is measured in the spine through a lumbar puncture. Increases in ICP have also been shown to occur with placement of tight fitting neck stabilization collars that likely compress the IJVs. Compression of the IJVs, which can occur when wearing shirts with tight collars or neckties, has also been shown to increase IOP. Notably, only mild compressive pressure is required to partially occlude the IJVs as they are a low pressure system. As the inflow of cerebral arterial blood continues after partial cerebral venous outlet obstruction, the intracerebral and venous pressure increases until the jugular venous resistance is overcome or the blood drainage is redirected to other venous channels. In either case there is a reduction in intracranial compliance and a modest increase in ICP.

The immunohistochemical assay used in the studies of the present disclosure is specific for axonal damage and results in a reliable range of measured damaged neurons. In addition, the Marmarou model of acceleration-deceleration injury is an accepted and well-studied methodology by which to quantify the extent of TBI. The reduction in damaged axons, as evidenced by a marked reduction in APP counts, in the experimental group with the IJV compression device is highly statistically significant (p<0.01). Additionally, the change in ICP was measured after applying the collar in five rats. The results show that every study rat had a reduction in axonal injury greater than the 95% confidence interval of the control group.

In a further aspect of the present invention it has been found that applying compression to the internal jugular vein not only reduces the risk of TBI, but also the risk of damage to the inner ear, spinal cord and structures of the eye. With respect to the ear, reducing IJV outflow will congest the cochlear vein and thereby take up the compliance of the inner ear or more particularly the fluid within the inner ear. Since the auditory hair cells react directly to the vibrations in the cochlear fluid, they are particularly susceptible to SLOSH energy absorption. Increasing the pressure of the fluid within the inner ear reduces the compressibility of the fluid within the inner ear structure so that blast energy is transmitted mechanically through the inner ear rather than absorbed by it in the form of vibration of the fluid. It is noted that increase the fluid pressure does not generally reduce transverse vibrations of the cochlear duct so the transmission of blast energy through the inner ear may still lead to perforation of the eardrum. But in many cases ruptured ear drums will heal or can be repaired. On the other hand, SLOSH-related damage to the fine auditory hair cells does not heal and cannot be repaired. Even if mitigating internal fluid vibration from blast energy increases the incidence of eardrum rupture the methods disclosed herein significantly reduce the risk of permanent hearing dysfunction.

With respect to the spinal cord, it has been found that reducing applying the IJV pressure techniques described herein reduces the compliance of fluid along the spinal axis reduces the risk of blast-related spinal injury. The spinal injury mode is similar to the inner ear damage mode in that the spinal cord tracts may be regarded as the sensitive filaments in a fluid environment. Fluid vibration due to SLOSH can damage and may even sever spinal cord tissue. Increasing the CSF pressure by compression of the IJV according to the procedure disclosed herein will significantly reduce the CSF vibration due to blast energy. Moreover, increasing the CSF pressure increase the axial load-bearing capacity of the spinal column which can reduce the likelihood of collapse of the spinal column due to blast energy.

With respect to the structure of the eye, the injury mode is similar to that of the inner ear and spine in that vibrations of the vitreous humor can lead to permanent damage to the internal structure of the eye. As demonstrated by woodpecker increasing intraocular volume and pressure protects the internal structure of the eye. Using the compression band to apply pressure to the IJV as disclosed herein the intra-ocular pressure can be increased 36-60%. Safely and reversibly increasing CSF and thereby intra-ocular pressure using the compression band disclosed herein can prevent or at a minimum significantly reduce the vibration of the vitreous humor within the eye, thereby reducing the risk of blast-related damage.

Finally, as discussed above, the concussive events leading to TBI, has also been found to be a leading cause of anosmia (loss or impairment of olfactory function, i.e., sense of smell). Increasing intracranial pressure as described above can reduce the risk of TBI and the associated impairment of olfactory function. In the case of Breecher or bomb-sniffing dogs the collar may be sized to fit the neck of the animal and the pressure adjusted to account for the greater thickness of the neck at the IJV over that of a human subject.

The foregoing description addresses blast-related traumatic injuries to the intracranial cavity, such as TBI, and injuries to the inner ear, spinal cord and ocular structure. The compression devices disclosed herein may thus be worn by military personnel during battle and removed when not in combat. Although certainly less dramatic, certain sports can expose the intracranial cavity to concussive forces that create the risk of these same traumatic injuries, most notably football. The compression collar disclosed herein would be worn by the sports participant in the field of play. The embodiments of the collar disclosed herein are relatively non-intrusive and the "break away" feature described above eliminates the risk of the collar being inadvertently pulled.

What is claimed is:

1. A method for mitigating injury to an inner ear of a human subject, the method comprising:
    applying pressure to a neck vein of the human subject prior to and during a concussive event, the neck vein being selected from a group consisting of an external jugular vein, an internal jugular vein, and any combination thereof,
    wherein the pressure is sufficient to congest a cochlear vein of the human subject thereby reducing a compressibility of cochlear fluid within the inner ear of the human subject so that energy of the concussive event is not transmitted to auditory hair cells within the inner ear of the human subject through vibration of the cochlear fluid.

2. The method of claim 1, wherein the pressure is sufficient to congest the cochlear vein thereby increasing a volume of the cochlear fluid.

3. The method of claim 1, wherein the pressure is sufficient to congest the cochlear vein thereby increasing a pressure of the cochlear fluid.

4. The method of claim 1, wherein the pressure is sufficient to congest the cochlear vein thereby increasing a volume and a pressure of the cochlear fluid.

5. The method of claim 1, wherein the pressure applied to the neck vein is equivalent to a fluid pressure of 5-80 mm Hg.

6. The method of claim 1, wherein the pressure is applied by a compression device that is configured to be worn on a neck of the human subject and the compression device encircles the neck.

7. The method of claim 1, wherein the pressure is applied by a compression device that is configured to be worn on a neck of the human subject and the compression device partially encircles the neck.

8. The method of claim 1, wherein the pressure is applied by a compression device that is configured to be worn on a neck of the human subject and the compression device is a resilient arcuate band.

9. The method of claim 1, wherein the pressure is sufficient to increase intracranial blood volume.

10. A method for mitigating injury to an ocular structure of a human subject, the method comprising:
    applying pressure to a neck vein of the human subject prior to and during a blast event, the neck vein being selected from a group consisting of an external jugular vein, an internal jugular vein, and any combination thereof,
    wherein the pressure is sufficient to increase intra-ocular pressure so that transmission of energy of the blast event through vibration of a vitreous humor within the ocular structure of the human subject is reduced.

11. The method of claim 10, wherein the pressure applied to the neck vein is equivalent to a fluid pressure of 5-80 mm Hg.

12. The method of claim 10, wherein the pressure is applied by a compression device that is configured to be worn on a neck of the human subject and the compression device encircles the neck.

13. The method of claim 10, wherein the pressure is applied by a compression device that is configured to be worn on a neck of the human subject and the compression device partially encircles the neck.

14. The method of claim 10, wherein the pressure is applied by a compression device that is configured to be worn on a neck of the human subject and the compression device is a resilient arcuate band.

15. The method of claim 10, wherein the pressure is sufficient to increase intracranial blood volume.

16. A method for mitigating injury to a brain of a human subject, the method comprising:
    applying pressure to a neck vein of the human subject prior to and during a blast event or concussive event, the neck vein being selected from a group consisting of an external jugular vein, an internal jugular vein, and any combination thereof,
    wherein the pressure is sufficient to restrict blood flow through the neck vein, thereby increasing intracranial pressure of the human subject so that absorption of energy of the blast event or concussive event to the brain is reduced.

17. The method of claim 16, wherein the pressure applied to the neck vein is equivalent to a fluid pressure of 5-80 mm Hg.

18. The method of claim 16, wherein the pressure is applied by a compression device that is configured to be worn on a neck of the human subject and the compression device encircles the neck.

19. The method of claim 16, wherein the pressure is applied by a compression device that is configured to be worn on a neck of the human subject and the compression device partially encircles the neck.

20. The method of claim 16, wherein the pressure is applied by a compression device that is configured to be worn on a neck of the human subject and the compression device is a resilient arcuate band.

21. A method for mitigating injury to a brain of a human subject, the method comprising:
applying pressure to a neck vein of the human subject prior to and during a blast event or concussive event, the neck vein being selected from a group consisting of an external jugular vein, an internal jugular vein, and any combination thereof,
wherein the pressure is sufficient to increase intracranial blood volume and to restrict blood flow through the neck vein, thereby increasing intracranial pressure of the human subject so that absorption of energy of the blast event or concussive event to the brain is reduced.

* * * * *